United States Patent [19]
Bachmaier et al.

[11] Patent Number: 5,962,636
[45] Date of Patent: Oct. 5, 1999

[54] PEPTIDES CAPABLE OF MODULATING INFLAMMATORY HEART DISEASE

[75] Inventors: Kurt Bachmaier; Andrew John Hessel, both of Toronto, Canada; Nickolaus Neu, Innsbruck, Austria; Josef Martin Penninger, Toronto, Canada

[73] Assignee: Amgen Canada Inc., Mississauga, Canada

[21] Appl. No.: 09/133,774

[22] Filed: Aug. 12, 1998

[51] Int. Cl.[6] ........................... A61K 38/00; A61K 38/04; A61K 39/02; A61K 39/00

[52] U.S. Cl. ...................... 530/326; 530/327; 424/190.1; 424/185.1

[58] Field of Search .................................... 530/326, 327; 424/190.1, 185.1

[56] References Cited

U.S. PATENT DOCUMENTS 5,252,714  10/1993  Harris et al. .

FOREIGN PATENT DOCUMENTS 0 154 316  3/1985  European Pat. Off. .
0 401 384  12/1989  European Pat. Off. .
WO 98/28005  7/1998  WIPO .

OTHER PUBLICATIONS

Penninger, J. M. et al. Cellular and molecular mechanisms of murine autoimmune myocarditis. APMIS v 105 pp. 1–13, Jan. 1997.

Allen, J.E. et al. Identification by sequence analysis of two–site postranslational processing of the cysteine–rich outer membrane protein 2 of Chlamydia trachomatis serovar L2. J. Bacteriol. vol. 171 pp. 285–291, Jan. 1989.

De La Maza, L.M. et al. Sequence diversity of the 60–kilodalton protein and of a putative 15–kilodalton protein between the trachoma and lymphogranuloma venerum biovars of *Chlamydia trachomatis*. Infection and Immunity v 59 pp. 1196–1201, Mar. 1991.

Watson, M.W. et al. The nucleotide sequence of the 60kDa cysteine rich outer membrane protein of *Chlamydia pneumoniae* strain IOL–207. Nucleic Acids Research vol. 18 p. 5299, 1990.

Watson, M.W. et al. The nucleotide sequence of the 60 kDa cysteine rich outer membrane protein of *Chlamydia psittaci* strain EAE/A22/M. Nucleic Acids Research vol. 18 p. 5300, 1990.

Hatt, C. et al. Analysis of the entire nucleotide sequence of the cryptic plasmid of *Chlamydia tachomatis* serovar L1: Evidence for involvement in DNA replication. Nucleic Acids Research v 16, pp. 4053–4067, 1988.

Ausubel et al., eds, *Current Protocols in Molecular Biology*, Green Publishers Inc. and Wiley and Sons, NY (1994) (Table of Contents Provided).

Ausubel et al., eds., "Metal–Chelate Affinity Chromatography", *Current Protocols in Molecular Biology*, Section 10.11.8, John Wiley & Sons, NY (1993).

Bodanszky, "Protection by Acylation", *Principles of Peptide Synthesis*, Springer–Verlag, New York p. 85 et seq. (1984).

Caruthers, "Gene Synthesis Machines: DNA Chemistry and Its Uses", *Science*, 230: 281–285 (1985).

Danesh et al., "Chronic infections and coronary heart disease: is there a link?", *Lancet*, 350: 430–436 (1997).

Davis et al., "CpG DNA Is a Potent Enhancer of Specific Immunity in Mice Immunized with Recombinant Hepatitis B Surface Antigen[1]", *J. Immunol.*, 160: 870–876 (1998).

Dayhoff et al., *Atlas of Protein Sequence and Structure*,5, supp. 3 (1978) (Table of Contents Provided).

de la Maza et al., "Sequence Diversity of the 60–Kilodalton Protein and of a Putative 15–Kilodalton Protein between the Trachoma and Lymphogranuloma Venereum Biovars of *Chlamydia trachomatis*", *Infect. Immun.*, 59: 1196–1201 (1991).

Engels et al., "Gene Synthesis", *Angew. Chem. Intl. Ed.*, 28: 716–734 (1989).

Francis, "Protein modification and fusion proteins", *Focus on Growth Factors*, 3: 4–10 (1992).

Genbank Accession No. M76598.

Gennaro, ed., *Remington's Pharmaceutical Sciences*, 18th Edition, Mack Publishing Company (1990) (Table of Contents Provided).

Houghten et al., "General method for the rapid solid–phase synthesis of large numbers of peptides: Specificity of antigen–antibody interaction at the level of individual amino acids", *Proc. Natl. Acad. Sci. USA*, 82: 5132 (1985).

Kitts et al., "A Method for Producing Recombinant Baculovirus Expression Vectors at High Frequency", *Biotechniques*, 14: 810–817 (1993).

Lucklow et al., "Efficient Generation of Infectious Recombinant Baculoviruses by Site–Specific Transposon–Mediated Insertion of Foreign Genes into a Baculovirus Genome Propagated in *Escherichia coli*", *J. Virol.*, 67: 4566–4579 (1993).

Lucklow, "Baculovirus systems for the expression of human gene products", *Curr. Opin. Biotechnol.*, 4: 564–572 (1993).

Marshall et al, "Oligonucleotide synthesis as a tool in drug discovery research", *Drug Discovery Today*, 3: 34–42 (1998).

Marston et al., "Solubilization of Protein Aggregates", *Meth. Enz.*, 182: 264–275 (1990).

Merrifield et al., "Solid Phase Peptide Synthesis. I. the Synthesis of a Tetrapeptide", *J. AM. Chem. Soc.*, 85: 2149 (1963).

Messina et al., "Stimulation of In Vitro Murine Lymphocyte proliferation by Bacterial DNA[1]", *J. Immunol*, 147: 1759–1764 (1991).

(List continued on next page.)

Primary Examiner—Frank C. Eisenschenk
Assistant Examiner—Ronald P Pelley
Attorney, Agent, or Firm—Nancy A. Oleski; Ron K. Levy; Steven M. Odre

[57] ABSTRACT

Disclosed are novel peptides that modulate inflammatory heart disease. Also disclosed are DNA molecules encoding the peptides, and methods of making the peptides.

7 Claims, No Drawings

OTHER PUBLICATIONS

Neu et al., "Cardiac Myosin Induces Myocarditis in Genetically Predisposed Mice[1]", *J. Immunol.,* 139: 3630–3636 (1987).

Penninger et al., "A Genetic Map of Autoimmune Heart Disease", *The Immunologist,* 4: 131–141 (1996).

Ossewaarde et al., "*Chlamydia pneumoniae* is a risk factor for coronary heart disease in symptom–free elderly men, but *Helicobacter pylori* and cytomegalovirus are not", *Epidemiol. and Infect.,* 120: 93–99 (1998).

Pummerer et al., "Identification of Cardiac Myosin Peptides Capable of Inducing Autoimmune Myocarditis in BALB/c Mice", *J. Clin. Invest.,* 97: 2057–2062 (1996).

Sambrook et al., *Molecular Cloning: A Laboratory Manual,* Cold Spring Harbor Laboratory Press, Cold Spring Harbor, NY (1989) (Table of Contents Provided).

Stein et al., "Physicochemical properties of phosphorothioate oligodeoxynucleotides", *Nuc. Acids Res.,* 16: 3209–3221 (1988).

Stewart and Young, Solid Phase Peptide Synthesis, Pierce Chemical Co., Rockford, IL (1984) (Table of Contents Provided).

SEQUENCE LISTING

<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<221> NAME/KEY: UNSURE
<222> LOCATION: (3)..(5)
<223> OTHER INFORMATION: Xaa's at above positions can be any amino acid.
<220> FEATURE:
<223> OTHER INFORMATION: Consensus sequence for myosin.

<400> SEQUENCE: 1

Met Ala Xaa Xaa Xaa Ser
 1               5

<210> SEQ ID NO 2
<211> LENGTH: 16
<212> TYPE: PRT
<213> ORGANISM: Mouse

<400> SEQUENCE: 2

Ser Leu Lys Leu Met Ala Thr Leu Phe Ser Thr Tyr Ala Ser Ala Asp
 1               5                  10                  15

<210> SEQ ID NO 3

```
<211> LENGTH: 14
<212> TYPE: PRT
<213> ORGANISM: Mouse

<400> SEQUENCE: 3

Ser Leu Lys Leu Leu Ser Asn Leu Phe Ala Asn Tyr Ala Gly
 1               5                  10

<210> SEQ ID NO 4
<211> LENGTH: 16
<212> TYPE: PRT
<213> ORGANISM: Chlamydia trachomatis

<400> SEQUENCE: 4

Val Leu Glu Thr Ser Met Ala Glu Phe Thr Ser Thr Asn Val Ile Ser
 1               5                  10                  15

<210> SEQ ID NO 5
<211> LENGTH: 16
<212> TYPE: PRT
<213> ORGANISM: Chlamydia trachomatis

<400> SEQUENCE: 5

Val Leu Glu Thr Ser Met Ala Glu Ser Leu Ser Thr Asn Val Ile Ser
 1               5                  10                  15

<210> SEQ ID NO 6
<211> LENGTH: 16
<212> TYPE: PRT
<213> ORGANISM: Chlamydia trachomatis

<400> SEQUENCE: 6

Val Leu Glu Thr Ser Met Ala Glu Phe Ile Ser Thr Asn Val Ile Ser
 1               5                  10                  15

<210> SEQ ID NO 7
<211> LENGTH: 16
<212> TYPE: PRT
<213> ORGANISM: Chlamydia pneumoniae

<400> SEQUENCE: 7

Gly Ile Glu Ala Ala Val Ala Glu Ser Leu Ile Thr Lys Ile Val Ala
 1               5                  10                  15

<210> SEQ ID NO 8
<211> LENGTH: 16
<212> TYPE: PRT
<213> ORGANISM: Chlamydia psittaci

<400> SEQUENCE: 8

Lys Ile Glu Ala Ala Ala Ala Glu Ser Leu Ala Thr Arg Phe Ile Ala
 1               5                  10                  15

<210> SEQ ID NO 9
<211> LENGTH: 14
<212> TYPE: PRT
<213> ORGANISM: Chlamydia trachomatis

<400> SEQUENCE: 9

Met Gly Ser Met Ala Phe His Lys Ser Arg Leu Phe Leu Thr
 1               5                  10

<210> SEQ ID NO 10
<211> LENGTH: 20
<212> TYPE: DNA
<213> ORGANISM: Chlamydia trachomatis
```

```
<220> FEATURE:
<223> OTHER INFORMATION: An oligonucleotide derived from the DNA
      encoding a 60 kDa cysteine rich outer membrane protein from
      Chlamydia trachomatis.

<400> SEQUENCE: 10
gattgcctga cgtcagagag                                                    20

<210> SEQ ID NO 11
<211> LENGTH: 20
<212> TYPE: DNA
<213> ORGANISM: Chlamydia trachomatis
<220> FEATURE:
<223> OTHER INFORMATION: An oligonucleotide derived from the DNA
      encoding a 60 kDa cysteine rich outer membrane protein from
      Chlamydia trachomatis.

<400> SEQUENCE: 11
tccatgacgt tcctgatgct                                                    20

<210> SEQ ID NO 12
<211> LENGTH: 20
<212> TYPE: DNA
<213> ORGANISM: Chlamydia trachomatis
<220> FEATURE:
<223> OTHER INFORMATION: An oligonucleotide derived from the DNA
      encoding a 60 kDa cysteine rich outer membrane protein from
      Chlamydia trachomatis.

<400> SEQUENCE: 12
tccatgacgt tcctgacgtt                                                    20

<210> SEQ ID NO 13
<211> LENGTH: 20
<212> TYPE: DNA
<213> ORGANISM: Chlamydia trachomatis
<220> FEATURE:
<223> OTHER INFORMATION: Oligonucleotide derived from the DNA
      encoding a 60 kDa cysteine rich outer membrane protein from
      Chlamydia trachomatis containing a CpG motif and referred to as a
      CpG oligo.

<400> SEQUENCE: 13
gtactgacgt ttactcttgg                                                    20

<210> SEQ ID NO 14
<211> LENGTH: 20
<212> TYPE: DNA
<213> ORGANISM: Chlamydia trachomatis
<220> FEATURE:
<223> OTHER INFORMATION: An oligonucleotide derived from the DNA
      encoding a 60 kDa cysteine rich outer membrane protein from
      Chlamydia trachomatis which does not contain the CpG motif and
      referred to as a non-CpG oligo.

<400> SEQUENCE: 14
gtactgagct ttactcttgg                                                    20

<210> SEQ ID NO 15
<211> LENGTH: 14
<212> TYPE: PRT
<213> ORGANISM: Human

<400> SEQUENCE: 15

Leu Lys Leu Leu Ser Thr Leu Phe Ala Asn Tyr Ala Gly Ala
 1               5                  10

<210> SEQ ID NO 16
```

```
<211> LENGTH: 14
<212> TYPE: PRT
<213> ORGANISM: Human

<400> SEQUENCE: 16

Ser Leu Lys Leu Met Ala Thr Leu Phe Ser Ser Tyr Ala Thr
 1               5                  10

<210> SEQ ID NO 17
<211> LENGTH: 48
<212> TYPE: DNA
<213> ORGANISM: Chlamydia trachomatis

<400> SEQUENCE: 17
gtgttagaga cctctatggc agagttcacc tctacaaacg ttattagc            48

<210> SEQ ID NO 18
<211> LENGTH: 48
<212> TYPE: DNA
<213> ORGANISM: Chlamydia trachomatis

<400> SEQUENCE: 18
gtgttagaga cctctatggc agagtctctc tctacaaacg ttattagc            48

<210> SEQ ID NO 19
<211> LENGTH: 48
<212> TYPE: DNA
<213> ORGANISM: Chlamydia trachomatis

<400> SEQUENCE: 19
gtgttagaga cctctatggc agagtttatc tctacaaacg ttattagc            48

<210> SEQ ID NO 20
<211> LENGTH: 48
<212> TYPE: DNA
<213> ORGANISM: Chlamydia pneumoniae

<400> SEQUENCE: 20
ggtatagagg ccgctgtagc agagtctctg attactaaga tcgtcgtc            48

<210> SEQ ID NO 21
<211> LENGTH: 48
<212> TYPE: DNA
<213> ORGANISM: Chlamydia psittaci

<400> SEQUENCE: 21
aagatagagg ccgctgctgc agagtctctt gctacaagat tcattgcc            48

<210> SEQ ID NO 22
<211> LENGTH: 42
<212> TYPE: DNA
<213> ORGANISM: Chlamydia trachomatis

<400> SEQUENCE: 22
atgggctcga tggctttcca taaaagtagg ttgttcttaa ct                  42

<210> SEQ ID NO 23
<211> LENGTH: 48
<212> TYPE: DNA
<213> ORGANISM: Mouse

<400> SEQUENCE: 23
tccctcaagc tcatggctac actcttctct acctatgctt ctgctgat            48
```

```
<210> SEQ ID NO 24
<211> LENGTH: 42
<212> TYPE: DNA
<213> ORGANISM: Human

<400> SEQUENCE: 24
tccctcaagc tcatggccac tctcttctcc tcctacgcaa ct                42

<210> SEQ ID NO 25
<211> LENGTH: 42
<212> TYPE: DNA
<213> ORGANISM: Mouse

<400> SEQUENCE: 25
tccctcaagc tcctaagtaa tctgtttgcc aactatgctg ga                42

<210> SEQ ID NO 26
<211> LENGTH: 42
<212> TYPE: DNA
<213> ORGANISM: Human

<400> SEQUENCE: 26
ctcaagttgc tcagcaccct gtttgccaac tatgctgggg ct                42
```

PEPTIDES CAPABLE OF MODULATING INFLAMMATORY HEART DISEASE

BACKGROUND

1. Field of the Invention

This invention relates to novel peptides, and to genes encoding the peptides, which are capable of inducing inflammatory cardiomyopathy in vivo.

2. Related Art

Cardiovascular diseases are a major cause of death in Western societies. Various risk factors have been associated with the pathogenesis of cardiovascular disease, including such factors as high cholesterol levels, smoking, stress, high blood pressure, obesity, and hyperglycemia. Recent evidence suggests that certain bacterial infections may be a causative event in the development of certain heart diseases (Danesh et al., *Lancet,* 350: 430–436 [1997]). In particular, Chlamydia infections have recently been shown to be linked, both epidemiolgcally and experimentally, to heart disease (Danesh et al., supra; Ossewaarde et al., *Epidemiol. and Infect.,* 120: 93–99 [1998]).

Inflammatory heart disease and dilated cardiomyopathy similar to that which occurs in humans can be induced in mice by immunization of the mice with myosin protein obtained from heart muscle (Neu et al., *J. Immunol.,* 139: 3630–3636 [1987]). Immunization of Balb/c mice with a peptide consisting of amino acids 614–643 of cardiac alpha-myosin can induce inflammatory heart disease in the mice (Pummerer et al., *J. Clin Invest.,* 97: 2057–2062 [1996]).

In view of the prevalence and devastating effects of cardiovascular disease, it would be beneficial to identify compounds that decrease the risk of inflammatory cardiomyopathy and methods of decreasing or preventing such disease.

Accordingly, it is an object of the present invention to provide novel compounds that are useful in decreasing and/or preventing inflammatory cardiomyopathy. Other such objects will be readily apparent to the skilled artisan.

SUMMARY OF THE INVENTION

In one embodiment, the present invention provides an isolated nucleic acid molecule encoding a peptide capable of inducing inflammatory cardiomyopathy selected from the group consisting of the nucleic acid molecules of SEQ ID NO:17, SEQ ID NO: 18, SEQ ID NO:19, SEQ ID NO:20, SEQ ID NO:21, SEQ ID NO:22, SEQ ID NO:23, and SEQ ID NO:24.

In another embodiment, the present invention provides a peptide capable of inducing inflammatory cardiomyopathy selected from the group consisting of: SEQ ID NO:2, SEQ ID NO:4, SEQ ID NO:5, SEQ ID NO:6, SEQ ID NO:7, SEQ ID NO:8, SEQ ID NO:9, and 16. Optionally, the peptide may be acylated at the amino terminus, and preferably acylation is by means of acetylation.

In yet another embodiment, the invention provides a vaccine comprising the peptide of SEQ ID NO:3 or SEQ ID NO:15. Optionally, the vaccine may further comprise an oligodeoxynucleotide selected from the group consisting of: SEQ ID NO:10, SEQ ID NO:11, SEQ ID NO:12, and SEQ ID NO:13.

In a further embodiment, the invention comprises a method of decreasing or preventing inflammatory cardiomyopathy comprising administering to a mammal in need thereof the peptide of SEQ ID NO:3 or SEQ ID NO:15.

The invention further comprises a method of inducing inflammatory myocarditis in a mammal comprising administering to the mammal the peptide of any of SEQ ID NO:2, SEQ ID NO:4, SEQ ID NO:5, SEQ ID NO:6, SEQ ID NO:7, SEQ ID NO:8, SEQ ID NO:9, and SEQ ID NO:16.

Yet further, the invention comprises a method for measuring the risk of inflammatory cardiomyopathy in a mammal, comprising incubating a sample of the mammal's T-cells with the peptide of any of SEQ ID NO:2, SEQ ID NO:4, SEQ ID NO:5, SEQ ID NO:6, SEQ ID NO:7, SEQ ID NO:8, SEQ ID NO:9, and SEQ ID NO:16.; measuring the proliferation of the T-cells; and comparing proliferation of the T-cell sample with control cells, wherein a higher level of proliferation as compared to control cells indicates an increased risk of inflammatory cardiomyopathy.

Still further, the invention comprises an isolated nucleic acid molecule comprising the nucleic acid molecule of SEQ ID NO:25 or SEQ ID NO:26, and peptides encoded by such nucleic acid molecules such as those of SEQ ID NO: 25 or SEQ ID NO:26.

The invention further provides vaccines comprising the peptides of SEQ ID Nos: 2, 4, 5, 6, 7, 8, 9, and 16.

Still further, the invention provides a method for measuring the risk of inflammatory cardiomyopathy in a mammal, comprising measuring the level of antibodies directed against one or more inflammatory cardiomyopathy peptides in the serum of the mammal, and comparing such antibody level to that contained in control serum, where an increase in antibodies as compared with control serum indicates an increased risk of inflammatory cardiomyopathy.

DETAILED DESCRIPTION OF THE INVENTION

Included in the scope of the present invention are novel peptides that can induce inflammatory heart disease in vivo. DNA molecules encoding these peptides, methods for preparing these peptides, and methods of using these peptides. Also within the scope of the present invention are novel peptides which decrease, or prevent inflammatory cardiomyopathy, as well as DNA molecules encoding these peptides, methods for preparing these peptides, and methods of using these peptides.

Also contemplated within the scope of the present invention are non-human mammals in which inflammatory cardiomyopathy has been induced via administration of one or more of the peptides of the present invention. Such non-human mammals are preferably chimpanzees or monkeys, pigs, dogs, rabbits, goats, sheep, or rodents such as mice or rats. Most preferred are rabbits, mice, and rats.

The scope of the present invention further includes an assay for determining the risk of inflammatory cardiomyopathy wherein blood is screened for the presence of activated T-cells and/or circulating antibodies directed to the novel peptides of the present invention.

The scope of the present invention further includes certain oligodeoxynucleotides that act as potent stimulators of the immune system.

A fragment of the alpha-myosin chain protein has been identified that can induce autoimmune inflammatory cardiomyopathy in vivo. In contrast, a homologous region of beta-myosin chain protein does not induce autoimmune inflammatory cardiomyopathy, and has been shown to prevent autoimmune inflammatory cardiomyopathy. An amino acid sequence comparison of the homologous peptides of the alpha and beta chains of myosin indicates that the motif MAxxxS (SEQ ID NO:1) is important for pathogenicity in vivo. Surprisingly, a search of public databases using SEQ ID NO:1 has identified various peptides from cysteine rich outer membrane proteins ("CRPs") of *Chlamydia trachomatis* that match the motif of SEQ ID NO:1. In addition, CRPs from *Chlamydia psittaci* and *Chlamydia pneumoniae* also share sequence homology to SEQ ID NO:1. As described in the Examples herein, some of these peptides also induce inflammatory cardiomyopathy in vivo.

The term "inflammatory cardiomyopathy peptide" refers to any peptide of the present invention, including without limitation, the peptides of SEQ ID Nos: 2, 4, 5, 6, 7, 8, 9, and 16, that can induce inflammatory cardiomyopathy in mammals such as mice in vivo.

For purposes herein, "inflammatory cardiomyopathy" refers to inflammation of the heart as measured by an increased heart/body weight ratio as compared with such ratio for normal hearts, and/or infiltration of the heart tissue with mononuclear cells which are normally absent in normal heart tissue.

The term "therapeutic cardiomyopathy peptide" refers to any peptide of the present invention, including, without limitation, the peptides of SEQ ID Nos: 3 and 15, that can reduce or prevent inflammatory cardiomyopathy in mammals such as mice in vivo, whether administered alone or in combination with an inflammatory cardiomyopathy peptide.

The term "inflammatory cardiomyopathy peptide fragment" refers to a peptide that is less than 16 amino acids in length but which has biological activity consistent with that described herein for inflammatory cardiomyopathy peptides.

The term "therapeutic cardiomyopathy peptide fragment" refers to a peptide that is less than 14 amino acids in length but which has biological activity consistent with that described herein for therapeutic cardiomyopathy peptides.

The term "inflammatory cardiomyopathy peptide variant" refers to an inflammatory cardiomyopathy peptide whose amino acid sequence contains one or more amino acid sequence substitutions, deletions, and/or insertions as compared to the peptides of SEQ ID NOS 2 and 16. Preferred inflammatory cardiomyopathy peptide variants are those containing conservative changes or alanine at one or more of amino acid residues 1–5, 8–10, and/or 12–16 as compared with SEQ ID NOS:2 and 16.

The term "therapeutic cardiomyopathy peptide variant" refers to an therapeutic cardiomyopathy peptide whose amino acid sequence contains one or more amino acid sequence substitutions, deletions, and/or insertions as compared to the peptides of SEQ ID NOS 3 and 15. Preferred therapeutic cardiomyopathy peptide variants are those which contain a conservative change or alanine at one or more of amino acid residues 1–4, 8–9, and 12–13.

The term "inflammatory cardiomyopathy peptide derivative" refers to an inflammatory cardiomyopathy peptide, fragment, or variant that has been chemically modified, as for example, by addition of one or more polyethylene glycol, dextran, sugar, phosphate, Fc peptide, and/or other such molecules, where such molecule or molecules are not naturally attached to the inflammatory cardiomyopathy peptides.

The term "therapeutic cardiomyopathy peptide derivative" refers to a therapeutic cardiomyopathy peptide, fragment, or variant that has been chemically modified, as for example, by addition of one or more polyethylene glycol, dextran, sugar, phosphate, Fc peptide, and/or other such molecules, where such molecule or molecules are not naturally attached to the therapeutic cardiomyopathy peptides.

As used herein, the terms "nucleic acid molecule encoding an inflammatory cardiomyopathy peptide" and "inflammatory cardiomyopathy nucleic acid" refer to a nucleic acid molecule or fragment thereof that (a) has the nucleotide sequence as set forth in any of SEQ ID NOS:2, 4, 5, 6, 7, 8, 9, and 16; (b) has a nucleic acid sequence encoding a biologically active inflammatory cardiomyopathy peptide that is at least 70 percent identical, but may be greater than 70 percent, i.e., 75, 80, 85, 90, 95 percent, or even greater than 95 percent identical, to any of the peptides of SEQ ID NOS:2, 4, 5, 6, 7, 8, 9, and 16; (c) is a naturally occurring allelic variant of (a) or (b); (d) is a nucleic acid variant of (a)–(c) produced as provided for herein;(e) has a sequence that is complementary to (a)–(d); and/or (f) hybridizes to any of (a)–(e) under conditions of high stringency.

As used herein, the terms "nucleic acid molecule encoding a therapeutic cardiomyopathy peptide" and "therapeutic cardiomyopathy nucleic acid" refer to a nucleic acid molecule or fragment thereof that (a) has the nucleotide sequence as set forth in any of SEQ ID NOS: 25 or 26; (b) has a nucleic acid sequence encoding a biologically active therapeutic cardiomyopathy peptide that is at least 70 percent identical, but may be greater than 70 percent, i.e., 75, 80, 85, 90, 95 percent, or even greater than 95 percent identical, to any of the peptides of SEQ ID NOS:3 or 15; (c) is a naturally occurring allelic variant of (a) or (b); (d) is a nucleic acid variant of (a)–(c) produced as provided for herein; (e) has a sequence that is complementary to (a)–(d); and/or (f) hybridizes to any of (a)–(e) under conditions of high stringency.

Percent sequence identity can be determined by standard methods that are commonly used to compare the similarity in position of the amino acids of two peptides or polypeptides, or one peptide and one polypeptide. By way of example, using a computer algorithm such as BLAST, BLAST2, or FASTA, the two (poly)peptides for which the percent sequence identity is to be determined are aligned for optimal matching of their respective amino acids (the "matched span", which can include the full length of one or both sequences, or a pre-determined portion of one or both sequences). Each computer algorithm provides a "default" opening penalty and a "default" gap penalty, and a scoring matrix such as PAM 250 (for FASTA) or BLOSUM 62 (for BLAST algorithms). A preferred algorithm is BLAST2.

A standard scoring matrix (see Dayhoff et al., in: *Atlas of Protein Sequence and Structure*, vol. 5, supp.3 [1978]) can be used in conjunction with the computer algorithm. The percent identity can then be calculated by determining the percent identity using an algorithm contained in a program such as FASTA:

$$\frac{\text{Total number of identical matches}}{[\text{length of the longer sequence within the matched span}] + [\text{number of gaps introduced into the longer sequence in order to align the two sequences}]} \times 100$$

Peptides or polypeptides that are at least 70 percent identical will typically have one or more amino acid substitutions, deletions, and/or insertions as compared with wild type peptide. Usually, the substitutions of the native residue will be either to alanine residues, or to conservative amino acids so as to have little or no effect on the overall net charge, polarity, or hydrophobicity of the peptide. Conservative substitutions are set forth in Table I below.

TABLE I

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

The term "conditions of high stringency" refers to hybridization and washing under conditions that permit binding (or hybridization) of a nucleic acid molecule used for screening (where such nucleic acid molecule typically encodes an inflammatory or therapeutic cardiomyopathy peptide or fragment thereof) such as an oligonucleotide probe or cDNA molecule probe, to highly homologous DNA or RNA molecules. An exemplary high stringency wash solution is 0.2×SSC and 0.1 percent SDS used at a temperature of between 50° C.–65° C.

Where oligonucleotide probes are used for hybridization, one of the following two exemplary high stringency solutions may be used. The first of these is 6×SSC with 0.05 percent sodium pyrophosphate at a temperature of 35° C.–62° C., depending on the length of the oligonucleotide probe. For example, 14 base pair probes can be washed at 35–40° C., 17 base pair probes can be washed at 45–50° C., 20 base pair probes can be washed at 52–57° C., and 23 base pair probes can be washed at 57–63° C. The temperature can be increased 2–3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45–50° C.

As used herein, the term "effective amount" when used in conjunction with "inflammatory cardiomyopathy peptide", refers to the amount of inflammatory cardiomyopathy peptide necessary to induce an immune response in a patient, whether human or non-human, to which it is administered.

The term "effective amount" when used in conjunction with "therapeutic cardiomyopathy peptide" refers to the amount of such peptide necessary to decrease or prevent inflammatory cardiomyopathy in a patient, whether human or non-human, to which it is administered.

The term "CpG oligodeoxynucleotide" refers to an oligodeoxynucleotide containing the internal motif "GACGTT". Preferably, the CpG oligodeoxynucleotide will be about 20 nucleotides in length, but may range from about 14 to 30 or more nucleotides in length.

The inflammatory cardiomyopathy peptides, fragments, and/or derivatives thereof, as well as the therapeutic cardiomyopathy peptides, fragments, variants, and derivatives thereof, may be prepared by chemical synthesis methods (such as solid phase peptide synthesis) using techniques known in the art such as those set forth by Merrifield et al., (*J. Am. Chem. Soc.,* 85: 2149 [1963]), Houghten et al. (*Proc Natl Acad. Sci.* USA, 82: 5132 [1985]), and Stewart and Young (Solid Phase Peptide Synthesis, Pierce Chemical Co., Rockford, Ill. [1984]). Such peptides may be synthesized with or without a methionine on the amino terminus. These chemically synthesized inflammatory cardiomyopathy peptides and therapeutic cardiomyopathy peptides or fragments, variants, and derivatives, may be acylated at the amino terminus using standard procedures (see "Protection by Acylation" in: Bodanszky, *Principles of Peptide Synthesis*, Springer-Verlag, N.Y. [1984] p. 85 et seq.). A preferred acylation group is the acetyl group. Such peptides may be oxidized using standard methods to form disulfide bridges if desired. The inflammatory cardiomyopathy peptides and therapeutic cardiomyopathy peptides produced by chemical synthesis and optionally acylated are expected to have biological activity comparable to inflammatory cardiomyopathy peptides or therapeutic cardiomyopathy peptides produced recombinantly or purified from natural sources, and thus may be used interchangably with the corresponding recombinant or natural peptides.

Inflammatory cardiomyopathy peptides, therapeutic cardiomyopathy peptides, and fragments, variants, or derivatives thereof, can also be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, NY [1994]).

A gene or cDNA encoding full length alpha myosin chain polypeptide, full length beta myosin chain polypeptide or fragments thereof which contain the DNA encoding the corresponding M7A-alpha or M7A-beta peptides of the present invention may be obtained for example by screening suitable genomic or cDNA library (such as a human muscle tissue cDNA or genomic library), or by PCR amplification. Probes or primers useful for screening the library can be generated based on the sequences set forth herein, or based on information for other known genes or gene fragments from the same or a related family of genes, such as, for example, conserved motifs found in other related or homologous genes. In addition, where an alpha myosin chain protein, a beta myosin chain protein, or fragment thereof (which contains the nucleic acid sequence encoding an inflammatory cardiomyopathy peptide or therapeutic cardiomyopathy peptide) has been identified from one species, all or a portion of that gene may be used as a probe to identify homologous genes from other species, or to identify allelic variants of the same species. The probes or primers may be used to screen cDNA libraries from various tissue sources believed to express the protein from which the inflammatory cardiomyopathy peptide or therapeutic cardiomyopathy peptide is derived (such as alpha or beta myosin chain genes, Chlamydia outer membrane protein genes, etc). Typically, conditions of high stringency will be employed for screening to minimize the number of false positives obtained from the screen. Once the full length gene or the portion of the full length gene encoding an inflammatory cardiomyopathy peptide or the therapeutic cardiomyopathy peptide of the present invention has been obtained, restriction endonuclease digestion may be used to obtain the portion of the gene encoding only the desired cardiomyopathy peptide or fragment thereof. This gene fragment can then be inserted into a suitable expression vector (as described herein) to produce the cardiomyopathy peptide.

Another means to prepare a gene encoding inflammatory cardiomyopathy peptide or fragment thereof, or therapeutic cardiomyopathy peptide or fragment thereof, or to prepare a CpG oligodeoxynucleotide of the present invention, is to employ chemical synthesis using methods well known to the skilled artisan such as those described by Engels et al. (*Angew. Chem. Intl. Ed.*, 28: 716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry.

In some cases, it may be desirable to prepare nucleic acid and/or amino acid variants of any of the inflammatory or therapeutic cardiomyopathy peptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such nucleic acid variants. Other methods known to the skilled artisan may be used as well. Preferred nucleic acid variants are those containing nucleotide substitutions accounting for codon preference in the host cell that is to be used to produce the peptide. Other preferred variants are those encoding conservative amino acid changes as described above (e.g., wherein the charge or polarity of the naturally occurring amino acid side chain is not altered substantially by substitution with a different amino acid) as compared to wild type.

The gene, cDNA, or nucleic acid fragment encoding an inflammatory cardiomyopathy peptide or therapeutic cardiomyopathy peptide can be inserted into an appropriate expression or amplification vector using standard ligation techniques. The vector is typically selected to be functional in the particular host cell employed (i.e., the vector is compatible with the host cell machinery such that amplification of the alpha or beta myosin chain peptide gene and/or expression of the gene can occur). The gene, cDNA or fragment thereof encoding an inflammatory cardiomyopathy peptide or therapeutic cardiomyopathy peptide may be amplified/expressed in prokaryotic, yeast, insect (baculovirus systems) and/or eukaryotic host cells. Selection of the host cell will depend in part on whether the peptide or fragment thereof is to be glycosylated and/or phosphorylated. If so, yeast, insect, or mammalian host cells are preferable.

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the peptide or polypeptide to be expressed, and a selectable marker element. Each of these elements is discussed below. Optionally, the vector may contain a "tag" DNA sequence, i.e., an oligonucleotide molecule located at the 5' or 3' end of the peptide coding sequence; the oligonucleotide molecule encodes polyHis (such as hexaHis), or other "tag" such as FLAG, HA (hemaglutinin Influenza virus) or myc for which commercially available antibodies exist. This tag is typically fused to the peptide upon its expression, and can serve as an tag for affinity purification of the peptide from the host cell. Affinity purification can be accomplished, for example, by column chromatography using antibodies against the tag as an affinity matrix. Optionally, the tag can subsequently be removed from the purified inflammatory cardiomyopathy peptide by various means such as using suitable peptidases.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native alpha or beta myosin chain polypeptide 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the native or endogenous flanking sequence will have been previously identified by mapping and/or by restriction endonuclease digestion and can thus be isolated from the proper tissue source using the appropriate restriction endonucleases. In some cases, the full length nucleic acid molecule of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the endogenous 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the alpha myosin chain (poly)peptide. If the vector of choice does not contain an origin of replication site, one may be chemically synthesized based on a known sequence, and ligated into the vector.

The transcription termination element is typically located 3' of the end of the inflammatory cardiomyopathy peptide coding sequence and serves to terminate transcription of the inflammatory or therapeutic cardiomyopathy peptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the alpha myosin chain peptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for an inflammatory or therapeutic cardiomyopathy peptide to be secreted from the host cell, a signal sequence may be used to direct the peptide out of the host cell where it is synthesized. Typically, the signal sequence is positioned within the coding region of the nucleic acid molecule encoding the inflammatory or therapeutic cardiomyopathy peptide, or directly at the 5' end of the inflammatory or therapeutic cardiomyopathy peptide coding region. Many signal sequences have been identified, and any of them that are functional in the selected host cell may be used in conjunction with the gene encoding the inflammatory or therapeutic cardiomyopathy peptide. Therefore, the signal sequence may be homologous or heterologous to the gene encoding the inflammatory or therapeutic cardiomyopathy peptide. Additionally, the signal sequence nucleic acid molecule may be chemically synthesized using methods set forth above.

In many cases, transcription of the gene encoding the inflammatory or therapeutic cardiomyopathy peptide is increased by the presence of one or more introns in the vector; this is particularly true where the inflammatory or therapeutic cardiomyopathy peptide is produced in eukaryotic host cells, especially mammalian host cells. The introns used may be naturally occurring within the gene from which the inflammatory or therapeutic cardiomyopathy peptide is derived. Where the intron is not naturally occurring, the intron(s) may be obtained from another source. The position of the intron with respect to the 5' flanking sequence and the gene encoding the inflammatory or therapeutic cardiomyopathy peptide is generally important, as the intron must be transcribed to be effective. As such, where the gene inserted into the expression vector is a cDNA molecule, the preferred position for the intron is 3' to the transcription start site, and 5' to the polyA transcription termination sequence. Preferably for cDNA, the intron will be located on one side or the other (i.e., 5' or 3') of the cDNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from starting vectors such as commercially available vectors. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion of the final vectors.

Preferred vectors for practicing this invention are those which are compatible with bacterial, insect, and mammalian host cells. Such vectors include, inter alia, pCRII, pCR3, and pcDNA3 (Invitrogen Company, San Diego, Calif.), pBSII (Stratagene Company, LaJolla, Calif.), pET15b (Novagen, Madison, Wis.), pGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

After the vector has been constructed and a nucleic acid molecule encoding inflammatory or therapeutic cardiomyopathy peptide has been inserted into the proper site of the vector, the completed vector may be inserted into a suitable host cell for amplification and/or peptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize inflammatory cardiomyopathy peptide which can subsequently be collected from the culture medium (if the host cell secretes it into the medium) or directly from the host cell producing it (if it is not secreted). After collection, the peptide can be purified using methods such as molecular sieve chromatography, affinity chromatography, and the like.

Selection of the host cell for inflammatory or therapeutic cardiomyopathy peptide production will depend in part on whether the peptide is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active peptide is prepared by the cell. However, where the host cell does not synthesize biologically active peptide, the peptide may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for expression of the peptides of the present invention.

Additionally, where desired, insect cell systems may be utilized in the methods of the present invention. Such systems are described for example in Kitts et al. (*Biotechniques*, 14: 810–817 [1993]), Lucklow (*Curr. Opin. Biotechnol.*, 4: 564–572 [1993]) and Lucklow et al. (*J. Virol.*, 67: 4566–4579 [1993]). Preferred insect cells are Sf-9 and Hi5 (Invitrogen, Carlsbad, Calif.)

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The culture medium will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of inflammatory or therapeutic cardiomyopathy peptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the inflammatory or therapeutic cardiomyopathy peptide has been designed to be secreted from the host cells, the majority of peptide may be found in the cell culture medium. Peptides prepared in this way will typically not possess an amino terminal methionine, as it is removed during secretion from the cell. If however, the peptide is not secreted from the host cells, it will be present in the cytoplasm and/or the nucleus (for eukaryotic host cells) or in the periplasm (for gram negative bacteria host cells) and may have an amino terminal methionine.

For peptide situated in the host cell cytoplasm and/or nucleus, the host cells are typically first disrupted mechanically or with detergent to release the intra-cellular contents into a buffered solution. The peptide can then be isolated from this solution.

Purification of inflammatory or therapeutic cardiomyopathy peptide from solution can be accomplished using a variety of techniques. If the peptide has been synthesized such that it contains a tag such as Hexahistidine (cyclin E2/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing alpha or beta myosin chain peptide). For example, polyhistidine binds with great affinity and specificity to nickel, thus an affinity column of nickel (such as the Qiagen® nickel columns) can be used for purification of peptide/polyHis (see for example, Ausubel et al., eds., *Current Protocols in Molecular Biology*, Section 10.11.8, John Wiley & Sons, New York [1993]).

Where the inflammatory or therapeutic cardiomyopathy peptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the inflammatory or therapeutic cardiomyopathy peptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If the inflammatory or therapeutic cardiomyopathy peptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The peptide in its now soluble form can then be analyzed using gel electrophoresis, immunoprecipitation or the like. If it is desired to isolate the peptide, isolation may be accomplished using standard methods such as those set forth below and in Marston et al. (*Meth. Enz.*, 182: 264–275 [1990]).

If inflammatory or therapeutic cardiomyopathy peptide inclusion bodies are not formed to a significant degree in the periplasm of the host cell, the peptide will be found primarily in the supernatant after centrifugation of the cell homogenate, and the peptide can be isolated from the supernatant using methods such as those set forth below.

In those situations where it is preferable to partially or completely isolate the inflammatory or therapeutic cardiomyopathy peptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

Chemically modified inflammatory or therapeutic cardiomyopathy peptide compositions ('derivatives') are included within the scope of the present invention. The chemical moiety selected is typically water soluble so that the alpha myosin chain peptide does not precipitate in an aqueous environment, such as a physiological environment. The chemical moiety selected is usually modified to have a single reactive group, such as an active ester for acylation or an aldehyde for alkylation, so that the degree of polymerization may be controlled as provided for in the present methods. The chemical moiety may be of any molecular weight, and may be branched or unbranched. Included within the scope of inflammatory cardiomyopathy peptide moieties is a mixture of such moieties. Preferably, for therapeutic use of the end-product preparation, the moiety will be pharmaceutically acceptable.

The water soluble moiety or mixture thereof may be selected from the group consisting of, for example, polyethylene glycol (PEG), monomethoxypolyethylene glycol, dextran, cellulose, or other carbohydrate based polymers or oligomers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer or oligomer(s) selected should have a single reactive ester group. For reductive alkylation, the polymer or oligomer(s) selected should have a single reactive aldehyde group. A preferred reactive aldehyde is polyethylene glycol propionaldehyde, which is water stable, or mono (C1–C10) alkoxy or aryloxy derivatives thereof (see U.S. Pat. No. 5,252,714).

Pegylation of inflammatory or therapeutic cardiomyopathy peptide may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable conditions used to react a biologically active substance with an activated polymer molecule. Methods for preparing pegylated inflammatory cardiomyopathy peptide will generally comprise the steps of (a) reacting a peptide with polyethylene glycol (such as a reactive ester or aldehyde derivative of PEG) under conditions whereby the peptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Generally, the peptide-polymer moieties of the present invention are useful for the same purposes as those described herein for inflammatory cardiomyopathy peptide and therapeutic cardiomyopathy peptide molecules. However, the polymer/peptide molecules disclosed herein may have additional activities, such as enhanced or reduced biological activity, or other characteristics, such as increased or decreased half-life, as compared to the non-derivatized molecules.

An alternative to chemical modification to produce peptide derivatives is production of fusion peptides. Such fusion peptides can be prepared by attaching polyamino acids to the peptides. For example, the polyamino acid may be a carrier protein which serves to increase the half life or stability of the peptide such as serum albumin, in particular, human serum albumin, an antibody or portion thereof (such as the antibody constant region known as "Fc", and, in particular, human or humanized Fc), or other polyamino acid. Preparation of such fusion peptides is readily accomplished using known cloning and recombinant DNA methods such as those set forth herein.

The inflammatory cardiomyopathy peptides, therapeutic cardiomyopathy peptides, and fragments thereof, variants, and derivatives thereof, may be employed alone, together, or in combination with other pharmaceutical compositions. Such peptides, fragments, variants, and derivatives may be used in combination with each other, and/or with cytokines, growth factors, antibiotics, anti-inflammatories, and/or chemotherapeutic agents as is appropriate.

The therapeutic cardiomyopathy peptides, whether administered alone or in combination, may be useful as vaccines for preventing or decreasing both autoimmune inflammatory cardiomyopathy and inflammatory cardiomyopathy due to Chlamydia or other bacterial or viral infections that cause inflammatory cardiomyopathy.

Nucleic acid molecules encoding inflammatory or therapeutic cardiomyopathy peptides, fragments, and/or derivatives that do not themselves encode peptides that are biologically active may be useful as hybridization probes in diagnostic assays to test, either qualitatively or quantitatively, for the presence of Chlamydia spp. DNA or corresponding RNA in mammalian tissue or bodily fluid samples.

The inflammatory or therapeutic cardiomyopathy peptides, fragments, variants, and/or derivatives may be used to prepare antibodies using standard methods. Thus, antibodies that react with the inflammatory or therapeutic cardiomyopathy peptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will either be of human origin, or will be "humanized", i.e., prepared so as to prevent or minimize an immune reaction to the antibody when administered to a patient. The antibody fragment may be any fragment that is reactive with the inflammatory and therapeutic cardiomyopathy peptides of the present invention, such as, $F_{ab}$, $F_{ab'}$, etc. Also provided by this invention are the hybridomas generated by presenting an inflammatory or therapeutic cardiomyopathy peptide or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human alpha or beta myosin chain peptide of the present invention are also encompassed by this invention.

The antibodies may be used therapeutically. The antibodies may further be used for in vivo and in vitro diagnostic purposes, such as in labeled form to detect the presence of Chlamydia in a body fluid or cell sample.

Preferred antibodies are human antibodies, either polyclonal or monoclonal.

Various assays can be used to identify biologically active inflammatory or therapeutic cardiomyopathy peptides. Such assays include, for example, injection of one or more of such peptides into a mammal such as a mouse, followed by analysis of heart tissue for inflammatory cardiomyopathy. Such procedures are described in the Examples herein.

Pharmaceutical Compositions and Administration

Pharmaceutical compositions of the inflammatory and therapeutic cardiomyopathy peptides are within the scope of the present invention. Such compositions may comprise an effective amount of peptide, fragments, variants, or derivatives in admixture with a pharmaceutically acceptable carrier. The carrier material may be water for injection, preferably supplemented with other materials common in solutions for administration to mammals. Typically, an inflammatory or therapeutic cardiomyopathy peptide compound will be administered in the form of a composition comprising purified peptide, fragment, variant, or derivative in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

The inflammatory or therapeutic cardiomyopathy peptide compositions can be administered parenterally. Alternatively, the compositions may be administered intravenously or subcutaneously. When systemically administered, the compositions for use in this invention may be in the form of a pyrogen-free, parenterally acceptable aqueous solution. The preparation of such pharmaceutically acceptable peptide solutions, with due regard to pH, isotonicity, stability and the like, is within the skill of the art.

Formulations of inflammatory or therapeutic cardiomyopathy peptide compositions useful for practicing the present invention may be prepared for storage by mixing the selected composition having the desired degree of purity with optional physiologically acceptable carriers, excipients, or stabilizers (*Remington's Pharmaceutical Sciences*, 18th Edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight peptides or polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the inflammatory or therapeutic cardiomyopathy peptide composition(s) to be employed will depend, for example, upon the objectives such as the indication for which the peptide is being administered, the route of administration, and the condition of the patient. Accordingly, it will be necessary for the therapist to titer the dosage and modify the route of administration as required to obtain the optimal effect. A typical daily dosage may range from about 0.1 $\mu$g/kg to up to 100 mg/kg or more, depending on the factors mentioned above. Typically, a clinician will administer the peptide composition until a dosage is reached that achieves the desired effect. The peptide composition may therefore be administered as a single dose, or as two or more doses (which may or may not contain the same amount of peptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of indication under treatment, the age and general health of the recipient, will be able to ascertain proper dosing.

The peptide composition to be used for in vivo administration must be sterile. This is readily accomplished by filtration through sterile filtration membranes. Where the peptide composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

Screening Assays

Included in the scope of the present invention are methods of screening a mammal for susceptiblity to, or risk of, autoimmune or bacterial-induced inflammatory cardiomyopathy, comprising assaying a biological fluid obtained from the mammal for activated T-cells to, and/or antibodies against, any of the inflammaotry cardiomyopathy peptides of the present invention.

By way of example, an individual can be evaluated for circulating antibodies, or T-cells that have been primed against either endogenous myosin alpha chain peptides of the present invention (such antibodies or primed T-cells, if present, could indicate an increased chance of developing autoimmune inflammatory cardiomyopathy), or to peptides from Chlamydia outer membrane proteins (as described in the Examples below; the presence of such circulating antibodies or primed T-cells could indicate an increased chance of developing bacterial-induced inflammatory cardiomyopathy). Such evaluation can be accomplished by obtaining a sample of blood from the individual, lysing the red blood cells in the sample (using, for example, ammonium chloride), collecting white blood cells, and incubating the white blood cells with one or more inflammatory cardiomyopathy peptides of the present invention in the presence of radioactive thymidine or an equivalent thereof. The cells can be harvested and counted for radioactivity. Higher levels of radioactivity as compared with controls (where the controls comprise T-cells not primed against the peptides, i.e., not previously exposed to the peptides) would correlate to an increased risk of developing inflammaotry cardiomyopathy. Those individuals at risk could then be de-sensitized through the use of vaccine therapy using one or more inflammatory cardiomyopathy peptides of the present invention as an active component of the vaccine.

In a second type of screening assay, the serum component of a blood sample from an individual could be tested for the presence of antibodies against the inflammatory cardiomyopathy peptide(s) of the present invention using ELISA, Western blot, or other suitable technique to detect antibodies. The presence of such antibodies could indicate and increased risk of developing inflammatory cardiomyopathy, in which case the individual could be made tolerant of the peptides via vaccine therapy as described above.

Oligonucleotides as Adjuvants

Certain bacterial DNA molecules purportedly can have immunostimulatory effects in vivo and in vitro (Davis et al., *J. Immunol.* , 160: 870 –876 [1998]). However, prior to the present invention, it was not known that certain oligodeoxynucleotides having a CpG motif (GACGTT) could be useful as adjuvants for vaccines.

As described in Example 2 below, it has been found that certain oligonucleotides, when injected simultaneously with an inflammatory cardiomyopathy peptide of the present invention, can serve to increase the immunogenicity of the peptide. The sequences of such oligodeoxynucleotides are set forth below:

GATTGCCTGACGTCAGAGAG (SEQ ID NO:10)
TCCATGACGTTCCTGATGCT (SEQ ID NO:11)
TCCATGACGTTCCTGACGTT (SEQ ID NO:12)
GTACTGACGTTTACTCTTGG (SEQ ID NO:13)

These oligodeoxynucleoitdes can be prepared using standard methods for oligonucleotide synthesis such as the phosphoramidite method as described above (see also Marshall, W. S., *Drug Discovery Today,* 3: 34–42 [1998]). In some cases, phosphorothioate modification can increase the in vivo stability. Such modification is well known in the art, and can be accomplished using, for example, the procedures as described in Stein et al., *Nuc,. Acids Res.,* 16: 3209–3221 [1988] or Caruthers, *Science,* 230: 281–285 [1985].

EXAMPLES

EXAMPLE 1

Identification and Preparation of Peptides Inducing Inflammatory Cardiomyopathy

A peptide from a region of the murine alpha myosin heavy chain polypeptide (Genbank accession number M76598) was prepared using standard FMOC (fluorenylmethoxycarbonyl)/t-butyl based solid phase peptide chemistry (Pummerer et al., *J. Clin Invest.,* 97: 2057–2062 [1996]). This peptide, referred to as "M7A-alpha", has the following sequence:

SLKLMATLFSTYASAD (SEQ ID NO:2)

The DNA encoding this peptide is:

TCCCTCAAGCTCATGGCTACACTCT-
TCTCTACCTATGCTTCTGCTGAT (SEQ ID NO:23)

A fragment of this peptide, which contains amino acids 1–14, was evaluated for its ability to induce autoimmune inflammatory cardiomyopathy as follows. Twenty seven Balb/c mice of about 6 weeks of age were immunized twice on days 0 and 7 with Freund's complete adjuvant (FCA) containing about 100 microliters of about 500 micrograms/ml of the peptide (prepared synthetically using standard peptide synthesis procedures). The mice were analyzed for the presence of inflammatory cardiomyopathy 21 days after the initial injection. The mice were sacrificed, and the hearts were dissected out, treated with formalin, and paraffin embedded. The heart tissue was then sectioned into sections of approximately 4 micrometers thick. The sections were stained using conventional procedures with hematoxylin (to detect nuclei) and eosin. Tissue sections were then viewed microscopically, and the mononuclear cells (which are completely absent in normal heart tissue) in each section were counted. In addition, each section was viewed for cardiomyocyte damage (necrosis). Severity of inflammatory cardiomyopathy was then determined taking into account both the tissue damage and the amount of mononuclear cell infiltration. The following scale was used to assign severity. A score of 1.0 indicates that up to five percent of the tissue was damaged/infiltrated; a score of 2.0 indicates that 5–10 percent of the tissue was damaged/infiltrated; a score of 3.0 indicates that 10–20 percent of the tissue was damaged/infiltrated; and a score of 4.0 indicates that more than 20 percent of the tissue was damaged/infiltrated.

Results of the analysis indicated that 24 of the 27 mice had developed inflammatory cardiomyopathy.

To test the specificity of the peptide of SEQ ID NO:2 to cause inflammatory cardiomyopathy, a second peptide derived from a homologous region of the murine beta myosin heavy chain (referred to as "M7A-beta")was tested in an identical manner. This peptide has the following amino acid sequence:

SLKLLSNLFANYAG (SEQ ID NO:3)

The DNA sequence encoding this peptide is:

TCCCTCAAGCTCCTAAGTAATCT-
GTTTGCCAACTATGCTGGA (SEQ ID NO:25)

Nineteen Balb/c mice of about 6 weeks of age were injected with this peptide in a manner identical to that described above. Twenty one days after the initial injection, these mice were analyzed for inflammatory cardiomyopathy using the method described above, and none were found to have developed the disease.

The sequences of SEQ ID NOS: 2 and 3 were compared to identify those amino acid residues necessary to induce inflammatory cardiomyopathy. The following "consensus sequence" was generated:

MAxxxS (SEQ ID NO:1)

The GCG (Wisconsin Package) program LOOKUP was used to generate a list file of bacterial and viral sequences from the PIR public protein database. The list file was then searched using SEQ ID NO:1 to identify those bacterial and viral proteins containing this sequence motif.

Surprisingly, several peptides were found that are fragments of cysteine rich outer membrane proteins from various species of Chlamydia. The sequences of these peptides and the corresponding DNA sequences are set forth below.

*C. trachomatis* cysteine-rich outer membrane protein 1:

VLETSMAEFTSTNVIS (SEQ ID NO:4)

*C. trachomatis* cysteine-rich outer membrane protein 2: VLETSMAESLSTNVIS (SEQ ID NO:5)

*C. trachomatis* cysteine-rich outer membrane protein 3: VLETSMAEFISTNVIS (SEQ ID NO:6)

*C. pneumoniae* cysteine-rich outer membrane protein: GIEAAVAESLITKIVA (SEQ ID NO:7)

*C. psittaci* cysteine-rich outer membrane protein: KIEAAAAESLATRFIA (SEQ ID NO:8)

*C. trachomatis* protein 11: MGSMAFHKSRLFLT (SEQ ID NO:9)

The respective DNA sequences of these peptides are as follows:

GTGTTAGAGACCTCTATGGCAGAGT-TCACCTCTACAAACGTTATTAGC (SEQ ID NO:17)

GTGTTAGAGACCTCTATGGCA-GAGTCTCTCTCTACAAACGTTATTAGC (SEQ ID NO:18)

GTGTTAGAGACCTCTATGGCAGAGTT-TATCTCTACAAACGTTATTAGC (SEQ ID NO:19)

GGTATAGAGGCCGCTGTAGCA-GAGTCTCTGATTACTAAGATCGTCGTC (SEQ ID NO:20)

AAGATAGAGGCCGCTGCTGCA-GAGTCTCTTGCTACAAGATTCATTGCC (SEQ ID NO:21)

ATGGGCTCGATGGCTTTCCATAAAAG-TAGGTTGTTCTTAACT (SEQ ID NO:22)

Each of the above peptides was prepared using the standard FMOC chemistry procedure (see above)and acetylated at the amino terminus using standard chemistry methods, and injected into mice (along with the M7A-alpha peptide as a control) to determine whether these peptides could induce inflammatory cardiomyopathy. The procedure for injection was identical to that described above. The mice were sacrificed 21 days after the initial injection, and the hearts were dissected out and sectioned as described above.

The following scale was used to assign severity of inflammatory cardiomyopathy in response to peptide injection. A score of 1.0 indicates that up to about five percent of the tissue was damaged/infiltrated; a score of 2.0 indicates that about 5–10 percent of the tissue was damaged/infiltrated; a score of 3.0 indicates that about 10–20 percent of the tissue was damaged/infiltrated; and a score of 4.0 indicates that more than about 20 percent of the tissue was damaged/infiltrated. The results are shown in Table 1. For mouse M7A-alpha, the complete sequence of SEQ ID NO:2 was used.

Table 1

TABLE 1

| Peptide | Prevalence | Percent | Severity |
|---|---|---|---|
| mouse M7A-alpha | 18/21 | 86% | 2.9 [0.7] |
| *C. trach.* 1 CRP | 12/15 | 80% | 1.4 [9.4] |
| *C. trach.* 2 CRP | 7/8 | 88% | 1.3 [0.5] |
| *C. trach.* 3 CRP | 7/8 | 88% | 1.1 [0.6] |
| *C. pneum.* CRP | 6/10 | 60% | 1.1 [0.2] |

TABLE 1-continued

| Peptide | Prevalence | Percent | Severity |
|---|---|---|---|
| *C. psitt.* CRP | 5/10 | 50% | 1.0 [0] |
| *C. trach.* p11 | 4/8 | 50% | 1.0 [0] |

The numbers in parentheses under "Severity" are standard deviations.

As can be seen, mouse M7A-alpha and the three *C. trachomatis* peptides induced the highest level of disease, and mouse M7A-alpha generated the greatest severity of disease.

Separately, the human homolog of the murine M7A-alpha peptide was evaluated using the procedure described above. The sequence of this peptide is:

SLKLMATLFSSYAT (SEQ ID NO:16)

The DNA encoding this peptide has the following sequence:

TCCCTCAAGCTCATGGCCACTCTCT-TCTCCTCCTACGCAACT (SEQ ID NO:24)

This human peptide was found to induce inflammatory cardiomyopathy to about the same degree as murine M7A-alpha.

In a separate study, about 50–100 micrograms of both murine M7A-alpha and M7A-beta (SEQ ID Nos:2 and 3, respectively) peptides were simultaneously injected into mice. The mice did not develop inflammatory cardiomyopathy, suggesting that the M7A-beta peptide protects the mammal from developing inflammatory cardiomyopathy. Such results indicate that M7A-beta and related peptides (e.g., homologous peptides from other species, such as human [see SEQ ID NO:15] as well as conservative substitutions of these peptides) could be useful as vaccines to decrease or prevent inflammatory cardiomyopathy. In addition, the peptides of SEQ ID NOS: 7, 8, 9, and/or conservative variants of SEQ ID NO: 3, as well as the human homolog of murine M7A-beta, the sequence of which is set forth immediately below as SEQ ID NO:15, which have a lower incidence of inducing inflammatory myocarditis or do not induce inflammatory myocarditis at all can be used as vaccines.

LKLLSTLFANYAGA (SEQ ID NO:15)

The DNA encoding this peptide has the following sequence:

CTCAAGTTGCTCAGCACCCTGTTTGC-CAACTATGCTGGGCT (SEQ ID NO:26)

EXAMPLE 2

Oligodeoxynucleotides as Immunostimulators

An oligonucleotides derived from the DNA encoding a 60 kDa cysteine rich outer membrane protein from *Chlamydia trachomatis* (de la Maza et al., *Infect. Immun.,* 59: 1196–1201 [1991]) containing a CpG motif and referred to as a "CpG oligo" (SEQ ID NO:13), and its counterpart not containing the CpG motif, the "non-CpG oligo" (SEQ ID NO:14), were synthesized using standard phosphoramidite chemistry, and were phosphorothioate modified (Stein et al., supra; Caruthers et al., supra). The sequence of these is set forth below:

GTACTGACGTTACTCTTGG (SEQ ID NO:13)

GTACTGAGCTTTACTCTTGG (SEQ ID NO:14)

Balb/c mice were immunized at day 0 and day 7 with a solution containing about 50 micrograms of M7A-alpha peptide (SEQ ID NO:2) and about 10 nmol of the oligodeoxynucleotide of either SEQ ID NO:13 (CpG oligodeoxynucleotide) or SEQ ID NO:14 (non-CpG oligodeoxynucleotide), together with Freund's incomplete adjuvant. Negative control mice received about 10 nmol of the oligodeoxynucleotide of SEQ ID NO:13 without peptide, and positive control mice received about 50 micrograms of M7A-alpha peptide with complete Freund's adjuvant.

After 21 days, the mice were analyzed for the presence and severity of inflammatory heart disease as described in Example 1. The results are shown in Table 2 below.

TABLE 2

| Adjuvant | Peptide | Prevalence | Severity |
| --- | --- | --- | --- |
| CFA | M7A-alpha | 5/5 | 3.8 ± 0.4 |
| CPG | M7A-alpha | 5/5 | 1.2 ± 0.4 |
| non-CpG | M7A-alpha | 1/5 | 1.0 ± 0.0 |
| CpG | None | 0/5 | — |

Surprisingly, the CpG oligonucleotide plus M7A-alpha peptide induced inflammatory heart disease in the absence of Freund's complete adjuvant, indicating that this oligonucleotide, which contains the CpG motif, can serve as a potent immunostimulator. The oligonucleotide containing the non-CpG motif was hardly effective as an adjuvant. Other CpG oligodeoxynucleotides tested and found to be immunostimulatory include the oligos set forth in SEQ ID Nos:10–12 (see above).

EXAMPLE 3

Assessing the Risk of Inflammatory Cardiomyopathy

About 10 ml of blood is obtained from a patient suspected of being at risk for inflammatory cardiomyopathy. The blood is treated with ammonium chloride to lyse red blood cells, after which the sample is centrifuged to pellet white blood cells. The white blood cells are collected and added to about 2 ml of RPMI cell culture medium containing about 10 percent fetal calf serum, and about 1–100 micrograms of M7A-alpha peptide or a Chlamydia peptide (as set forth in Example 1) are then added. The cell sample is then incubated at about 37 C. and about 5 percent carbon dioxide for up to about 4 days in the presence of tritiated thymidine (about 1 micro Curie). The cells are then washed and counted for radioactivity.

Samples from patients previously exposed to Chlamydia, or have a proclivity towards autoimmune inflammatory myocarditis will show a higher level of T-cell proliferation as measured by higher levels of radioactivity when compared to white blood cell samples from individuals never exposed to Chalmydia or having no history of, nor proclivity to, autoimmune cardiomyopathy.

In an alternate procedure, blood from a patient can be obtained and centrifuged to collect the plasma. The plasma can then be tested via standard ELISA or other comparable procedure to assay for the presence of antibodies in the plasma that recognize any of the inflammatory cardiomyopathy peptides such as M7A-alpha or the Chlamydia peptides. Standards for the ELIZA can include plasma from individuals never exposed to Chalmydia or having no history of, nor proclivity to, autoimmune cardiomyopathy. When the sample serum antibody levels are compared with the standard serum antibody levels, a higher level of the antibodies as compared with the control serum indicates an increased risk of inflammatory cardiomyopathy.

We claim:

1. A peptide selected from the group consisting of: SEQ ID NO:2, SEQ ID NO:4, SEQ ID NO:5, SEQ ID NO:6, SEQ ID NO:7, SEQ ID NO:8, SEQ ID NO:9, and SEQ ID NO:16.

2. The peptide of claim 1 wherein the amino-terminal amino acid is acylated.

3. The peptide of claim 2 wherein an acetyl group is used for acylation.

4. A peptide selected from the group consisting of: SEQ ID NO:3 and SEQ ID NO:15.

5. The peptide of claim 4 wherein the amino-terminal amino acid is acylated.

6. The peptide of claim 5 wherein an acetyl group is used for acylation.

7. A vaccine to decrease inflammatory cardiomyopathy comprising a peptide, an adjuvant, and an excipient, wherein the peptide consists of any of SEQ ID NOS; 2, 3, 4, 5, 6, 7, 8, 9, 15, or 16.

* * * * *

UNITED STATES PATENT AND TRADEMARK OFFICE
CERTIFICATE OF CORRECTION

PATENT NO. : 5,962,636
DATED : OCTOBER 5, 1999
INVENTOR(S) : BACHMAIER, ET AL.

It is certified that error appears in the above-identified patent and that said Letters Patent is hereby corrected as shown below:

Column 19, line 64: In Table 1 under the column "Severity", line 2, change "1.4[9.4]" to -- 1.4[0.4] --

Signed and Sealed this

Twenty-fifth Day of July, 2000

Attest:

Q. TODD DICKINSON

*Attesting Officer*      *Director of Patents and Trademarks*